United States Patent
Iso et al.

(10) Patent No.: US 9,320,476 B2
(45) Date of Patent: Apr. 26, 2016

(54) X-RAY COMPUTED TOMOGRAPHY APPARATUS, RADIATION DETECTOR, AND METHOD OF MANUFACTURING RADIATION DETECTOR

(75) Inventors: Machiko Iso, Nasushiobara (JP); Yoshiaki Yaoi, Nasushiobara (JP); Keiji Matsuda, Nasushiobara (JP); Shuya Nambu, Nasushiobara (JP); Takashi Kanemaru, Nasushiobara (JP); Akihiko Taniguchi, Yokohama (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 210 days.

(21) Appl. No.: 13/239,843

(22) Filed: Sep. 22, 2011

(65) Prior Publication Data

US 2012/0069954 A1 Mar. 22, 2012

(30) Foreign Application Priority Data

Sep. 22, 2010 (JP) .................................. 2010-211667
Aug. 25, 2011 (JP) .................................. 2011-183452

(51) Int. Cl.
*G21K 1/12* (2006.01)
*A61B 6/03* (2006.01)
(Continued)

(52) U.S. Cl.
CPC ................ *A61B 6/03* (2013.01); *A61B 6/4291* (2013.01); *G21K 1/025* (2013.01); *G21K 2207/00* (2013.01); *Y10T 29/49826* (2015.01)

(58) Field of Classification Search
CPC .... G21K 1/02; G21K 1/025; G01N 2223/316
USPC .................................................. 378/147, 154
See application file for complete search history.

(56) References Cited

U.S. PATENT DOCUMENTS 5,949,850 A 9/1999 Tang
2004/0161074 A1* 8/2004 Kresse ................ G01V 5/0016
378/19

(Continued)

FOREIGN PATENT DOCUMENTS

CN 101027000 A 8/2007
JP 2007-47174 2/2007

(Continued)

OTHER PUBLICATIONS

Office Action issued Apr. 25, 2014, in China Patent Application No. 201110290355.5.

(Continued)

*Primary Examiner* — Hoon Song
(74) *Attorney, Agent, or Firm* — Oblon, McClelland, Maier & Neustadt, L.L.P.

(57) ABSTRACT

An X-ray CT apparatus according to an embodiment includes an X-ray detector and a collimator unit. The X-ray detector detects X-rays that have passed through a subject. The collimator unit eliminates scattered radiation from X-rays that are incident on the X-ray detector. The collimator unit includes a plurality of collimator modules, a supporter, and a fixing unit. The plurality of collimator modules each includes a plurality of first collimator plates arranged in a grid along a channel direction and a slice direction that are orthogonal to each other. The supporter supports the collimator modules such that the collimator modules are aligned in a plurality of straight lines along the channel direction and in a plurality of straight lines along the slice direction. The fixing unit is provided to the supporter and fixes positions of the collimator modules in the channel direction and the slice direction.

10 Claims, 13 Drawing Sheets

(51) Int. Cl.
*A61B 6/00* (2006.01)
*G21K 1/02* (2006.01)

(56) References Cited

U.S. PATENT DOCUMENTS

| | | | |
|---|---|---|---|
| 2006/0076498 A1* | 4/2006 | Hilderscheid | G01T 1/1648 250/370.09 |
| 2006/0124856 A1* | 6/2006 | Heismann | G01N 23/046 250/370.09 |
| 2007/0025519 A1* | 2/2007 | Vogtmeier et al. | 378/149 |
| 2008/0230706 A1* | 9/2008 | Dorscheid et al. | 250/363.05 |
| 2012/0132834 A1* | 5/2012 | Freund | G21K 1/025 250/505.1 |

FOREIGN PATENT DOCUMENTS

| | | |
|---|---|---|
| JP | 4510823 B2 | 5/2010 |
| JP | 2010-127630 A | 6/2010 |

OTHER PUBLICATIONS

Japanese Office Action issued Mar. 3, 2015 in Patent Application No. 2011-183452 (without English Translation).

* cited by examiner

X-RAY COMPUTED TOMOGRAPHY APPARATUS, RADIATION DETECTOR, AND METHOD OF MANUFACTURING RADIATION DETECTOR

CROSS-REFERENCE TO RELATED APPLICATIONS

This application is based upon and claims the benefit of priority from Japanese Patent Application No. 2010-211667, filed on Sep. 22, 2010; and Japanese Patent Application No. 2011-183452, filed on Aug. 25, 2011, the entire contents of all of which are incorporated herein by reference.

FIELD

Embodiments described herein relate generally to an X-ray computed tomography apparatus, a radiation detector, and a method of manufacturing a radiation detector.

BACKGROUND

Conventional radiation diagnostic apparatuses, such as an X-ray computed tomography (CT) apparatus, include a radiation detector that detects radiation, such as X-rays and γ rays. The radiation diagnostic apparatus generally includes a collimator that eliminates scattered radiation from radiation that is incident on the radiation detector. The collimator includes a one-dimensional collimator that eliminates scattered radiation from a channel direction and a two-dimensional collimator that eliminates scattered radiation from the channel direction and a slice direction (body axis direction).

Conventionally, by creating a collimator as a seamless assembly, a one-dimensional collimator is manufactured such that the thickness and pitch of its collimator plates are uniform. In contrast, for a two-dimensional collimator, because it is necessary to arrange collimator plates in two-dimensional directions, it is difficult to create a collimator for all the channels and slices as a seamless assembly. For this reason, for the two-dimensional collimator, a manufacturing method is used in which a plurality of collimator modules are created and arranged so as to be aligned in the channel direction and the slice direction.

However, in the conventional technology in which a plurality of collimator modules are arranged so as to be aligned, the thickness and pitch of the collimator plates are not always uniform. FIGS. 20 to 23 illustrate the problem in the conventional technology.

For example, when collimator modules 10 each with outer frames on all four sides, as shown in FIG. 20, are aligned, the thickness and pitch of the collimator plates are discontinuous in the channel direction (indicated by the arrow C) and the slice direction (indicated by the arrow S) in positions where collimator modules meet. Furthermore, for example, when collimator modules 20, as shown in FIGS. 22 and 23, each with outer frames on two sides are aligned such that the ends of the collimator plates, which are ends protruding on the sides with no outer frame, make contact with outer frames of adjacent modules, the pitch may be inconsistent between the modules due to manufacturing errors. The pitch error increases as the number of modules to be combined increases. As described above, in the conventional technology, the thickness and pitch of the collimator plates are not always uniform.

DETAILED DESCRIPTION

An X-ray CT apparatus according to an embodiment includes an X-ray detector and a collimator unit. The X-ray detector detects X-rays that have passed through a subject. The collimator unit eliminates scattered radiation from X-rays that are incident on the X-ray detector. The collimator unit includes a plurality of collimator modules, a supporter, and a fixing unit. The plurality of collimator modules each includes a plurality of first collimator plates arranged in a grid along a channel direction and a slice direction that are orthogonal to each other. The supporter supports the collimator modules such that the collimator modules are aligned in a plurality of straight lines along the channel direction and in a plurality of straight lines along the slice direction. The fixing unit is provided to the supporter and fixes positions of the collimator modules in the channel direction and the slice direction.

First Embodiment

Figure 1:
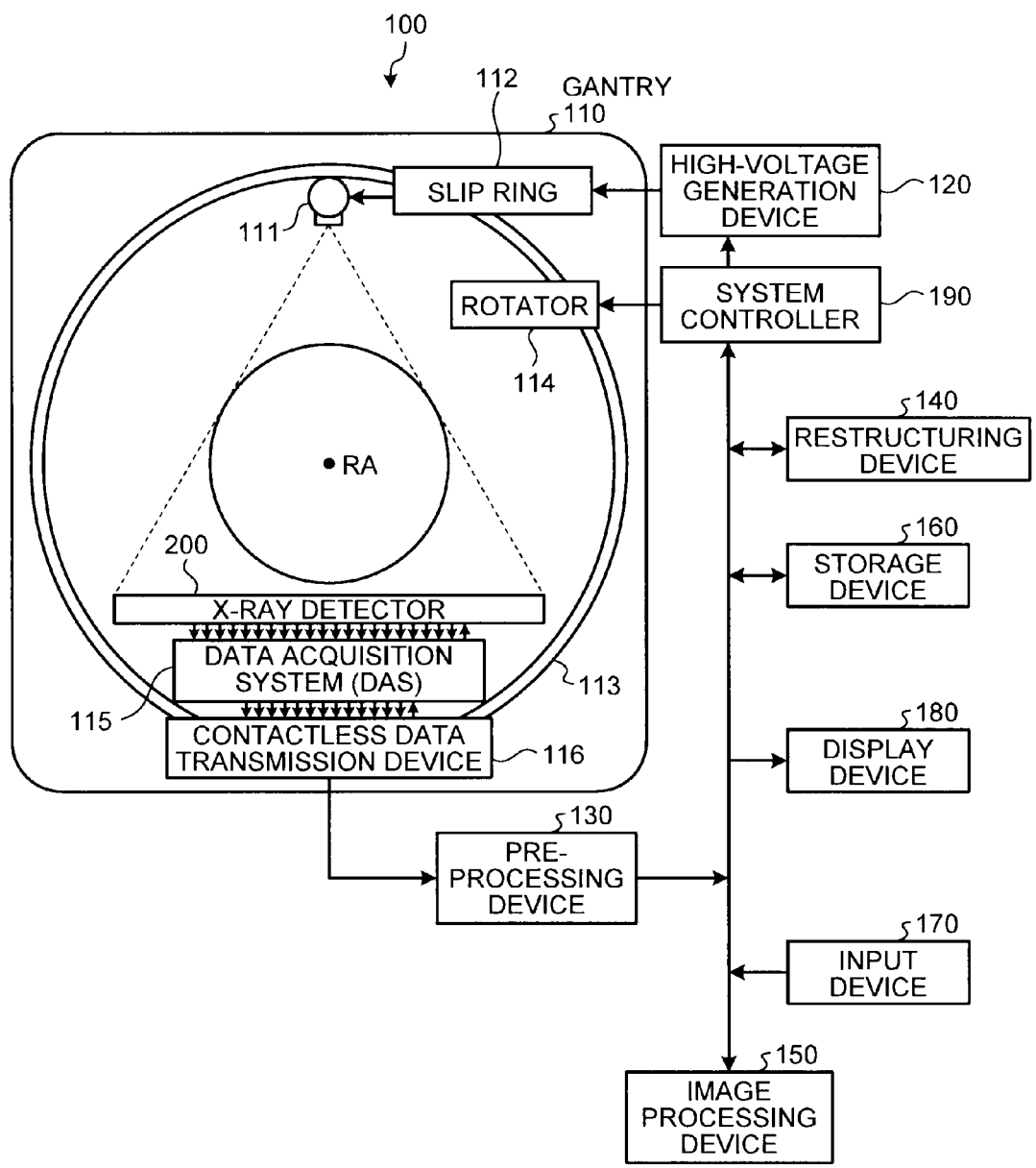
FIG. 1 is a diagram of a configuration of an X-ray CT apparatus according to a first embodiment.

A first embodiment will be described first. FIG. 1 is a diagram of a configuration of an X-ray CT apparatus 100 according to the first embodiment. As shown in FIG. 1, the X-ray CT apparatus 100 includes a gantry 110, a high-voltage generation device 120, a pre-processing device 130, a restructuring device 140, an image processing device 150, a storage device 160, an input device 170, a display device 180, and a system controller 190.

The gantry 110 irradiates a subject with X-rays, detects the X-rays that is transmitted through the subject, and generates raw data. The gantry 110 includes an X-ray tube 111, a slip ring 112, an X-ray detector 200, a flame 113, a rotator 114, a data acquisition system (DAS) 115, and a contactless data transmission device 116.

The X-ray tube 111 generates X-rays, with which a subject is irradiated, due to the tube voltage and tube current that are provided via the slip ring 112 from the high-voltage generation device 120. The X-ray detector 200 detects X-rays that were generated by an X-ray tube 11 and have been transmitted through the subject. The X-ray detector 200 will be described in detail below.

The frame 113 is annularly formed and is provided so as to be rotatable on a rotation axis RA. The frame 113 supports the X-ray tube 111 and the X-ray detector 200 so that they are opposed to each other with the rotation axis RA in between. The rotator 114 rotates the frame 113 on the rotation axis RA. For example, the rotator 114 rotates the frame 113 at a rate of one rotation every 0.4 seconds.

The DAS 115 collects signals indicating the X-rays detected by the X-ray detector 200, amplifies the signals, and converts the signals to digital signal data (raw data). The contactless data transmission device 116 transmits the raw data, which is output from the DAS 115, to the pre-processing device 130.

The high-voltage generation device 120 is a device that supplies a tube voltage and a tube current to the X-ray tube 111 of the gantry 110 in order to generate X-rays. The pre-processing device 130 generates projection data, from which an image is restructured, by performing a correction process, such as a sensitivity correction, on the raw data transmitted from the contactless data transmission device 116.

The restructuring device 140 restructures image data of the subject by performing a predetermined restructuring process on the projection data, which is generated by the pre-processing device 130. The image processing device 150 generates a three-dimensional image, a curve multi planar reconstruction (MPR) image, and a cross cut image, and the like, using the image data that is restructured by the restructuring device 140.

The storage device 160 stores the projection data that is generated by the pre-processing device 130, the image data that is restructured by the restructuring device 140, and various images that are generated by the image processing device 150. The storage device 160 is, for example, a hard disk drive (HDD) or a digital versatile disc (DVD) drive.

The input device 170 receives various operations on the X-ray CT apparatus 100 from an operator. The input device 170 is, for example, a keyboard and a mouse. The display device 180 outputs various images, which are generated by the restructuring device 140 or the image processing device 150, and outputs a graphical user interface (GUI) for receiving various operations from the operator. The display device 180 is, for example, a liquid crystal panel or a cathode ray tube (CRT) monitor.

The system controller 190 controls behavior of the whole X-ray CT apparatus 100 according to various operations received by the input device 170.

Figure 2:
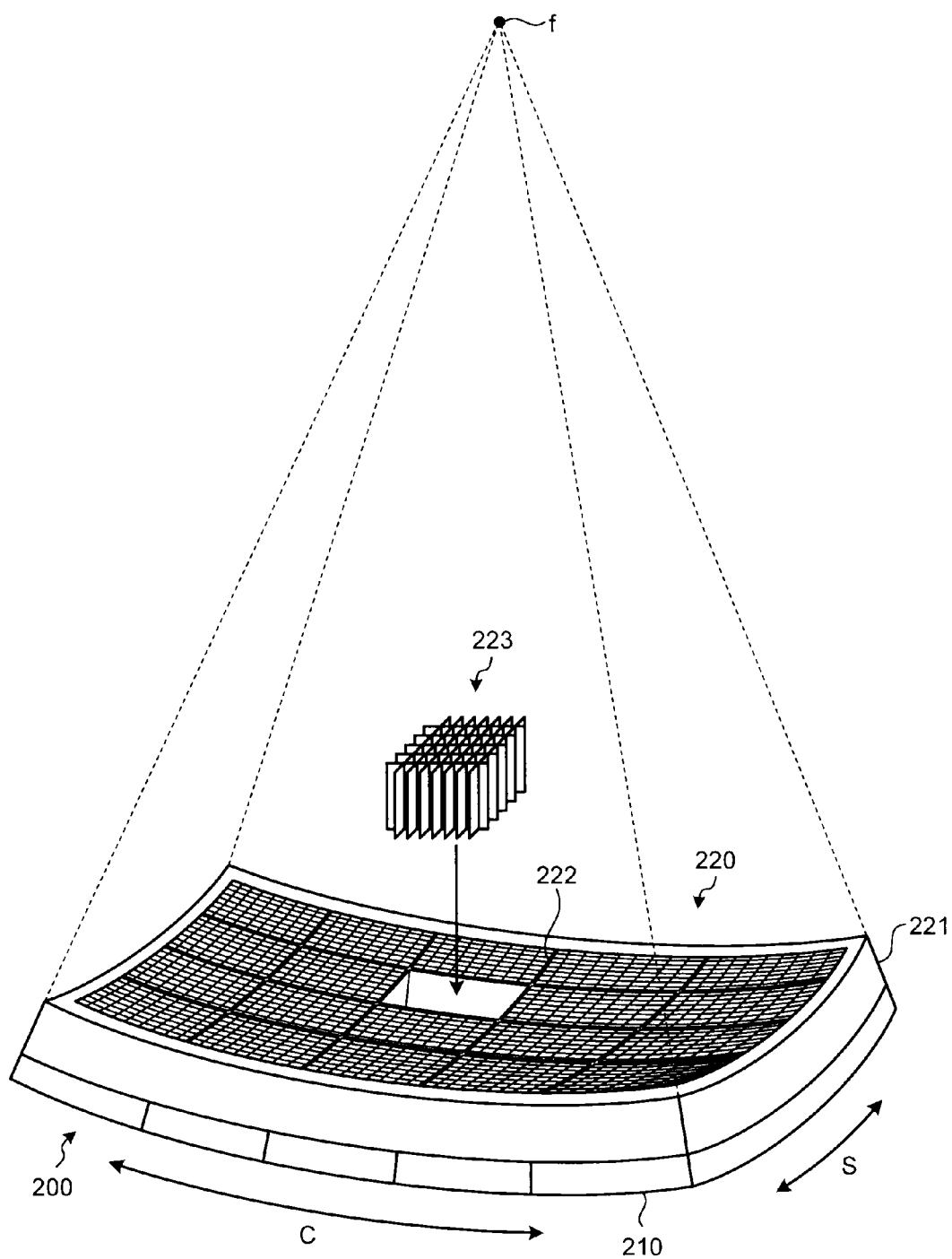
FIG. 2 is a diagram of a configuration of an X-ray detector in FIG. 1.

A configuration of the X-ray detector 200 in FIG. 1 will be described. FIG. 2 is a diagram of a configuration of the X-ray detector 200 in FIG. 1. As shown in FIG. 2, the X-ray detector 200 includes an X-ray detector 210 and a collimator unit 220. In FIG. 2, the arrow C denotes the channel direction. The arrow C denotes the slice direction (body axis direction) orthogonal to the channel direction.

The X-ray detector 210 detects X-rays that were generated by the X-ray tube 111 and have been transmitted through the subject. Specifically, the X-ray detector 210 includes a scintillator array, a photo diode (PD) array, and a circuit substrate. The scintillator array includes a plurality of scintillator blocks, which are arrayed in the channel direction and the slice direction, and generates fluorescence by receiving the X-rays. The PD array includes a plurality of photo diodes and converts the fluorescence, which is generated by the scintillator array, into electric signals. The circuit substrate absorbs the electric signals, which are converted by the PD array, and outputs the electric signals to the DAS 115.

The collimator unit 220 eliminates scattered radiation from X-rays incident on the X-ray detector 210. Specifically, the collimator unit 220 includes a collimator frame 221, a collimator base 222, and collimator modules 223.

The collimator frame 221 is formed to have an approximately rectangular shape and depth in the direction in which the X-rays are incident and is further formed so that it curves along a sphere about a focal point f of the X-ray tube 111. The collimator frame 221 holds the collimator base 222 and the collimator modules 223 within itself.

Figure 3:
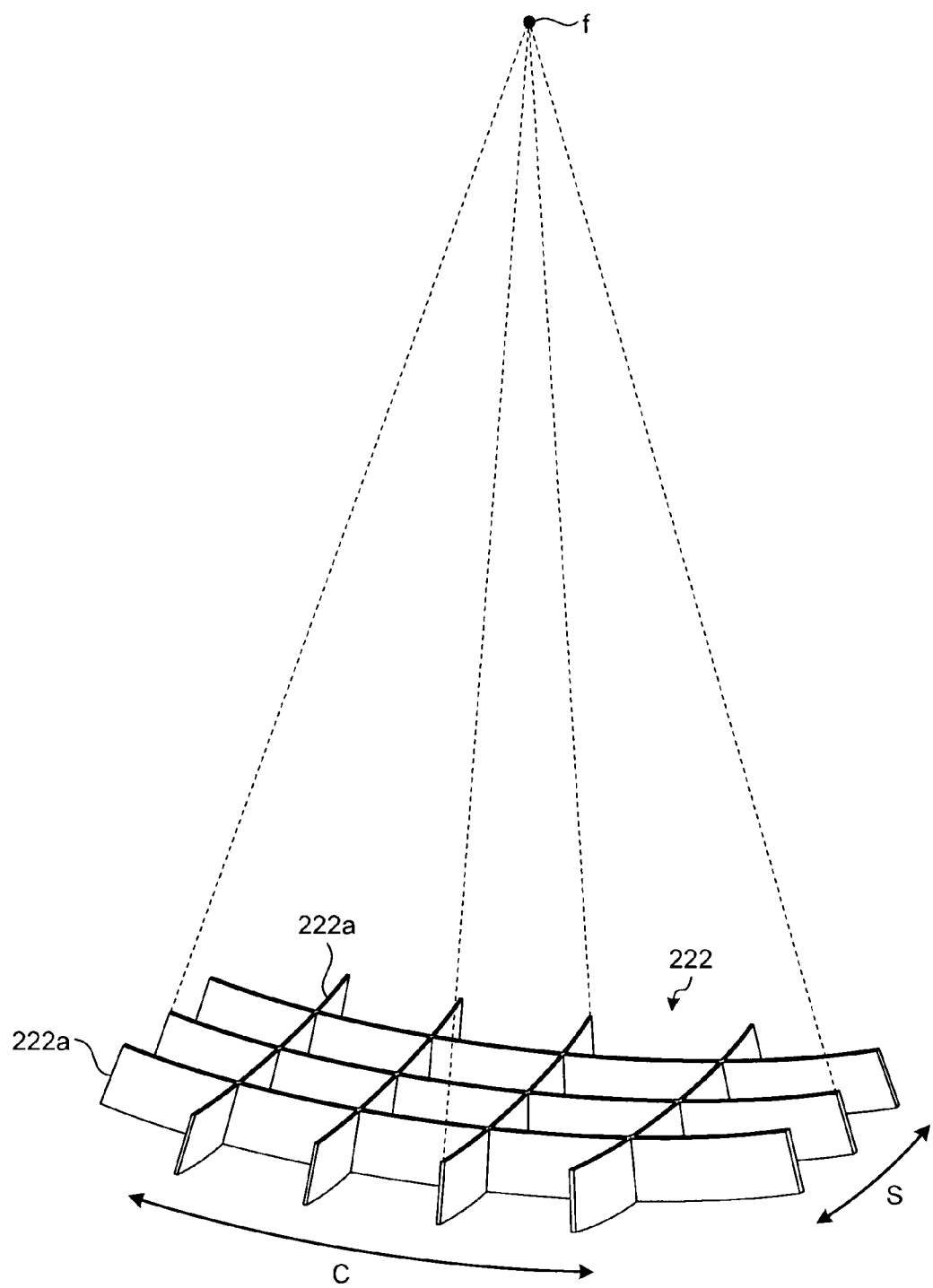
FIG. 3 is a diagram of an outer view of a collimator base in FIG. 2.

The collimator base 222 supports the collimator modules 223 such that the collimator modules 223 are arrayed in the channel direction and the slice direction. FIG. 3 is an outer view of the collimator base in FIG. 2. Specifically, as shown in FIG. 3, the collimator base 222 includes a plurality of collimator plates 222a that are arrayed in a grid such that the plurality of collimator plates 222a are aligned in the channel direction and the slice direction. As described above, by arraying the collimator plates 222a in a grid, a plurality of sections are formed in a matrix in the collimator base 222. In each of the sections, the collimator module 223, which will be described below, is housed.

Furthermore, as shown in FIG. 3, the collimator plates 222a are each formed into an arc and are arranged such that the centers of the arcs coincide at the focal point f of the X-ray tube 111. Accordingly, the whole collimator base 222 has a shape that curves along a sphere about the focal point f. Thus, when the collimator modules 223 are arranged respectively in the sections that are partitioned by the collimator plates 222a, each of the collimator modules 223 faces the focal point f.

The collimator modules 223 are arranged respectively in a plurality of sections, which are partitioned by the collimator plates 222a of the collimator base 222, and the collimator modules 223 eliminate the scattered radiation from the X-rays that are incident on the X-ray detector 210. FIGS. 4 to 7 are diagrams of a configuration of the collimator module 223 in FIG. 2.

Figure 4:
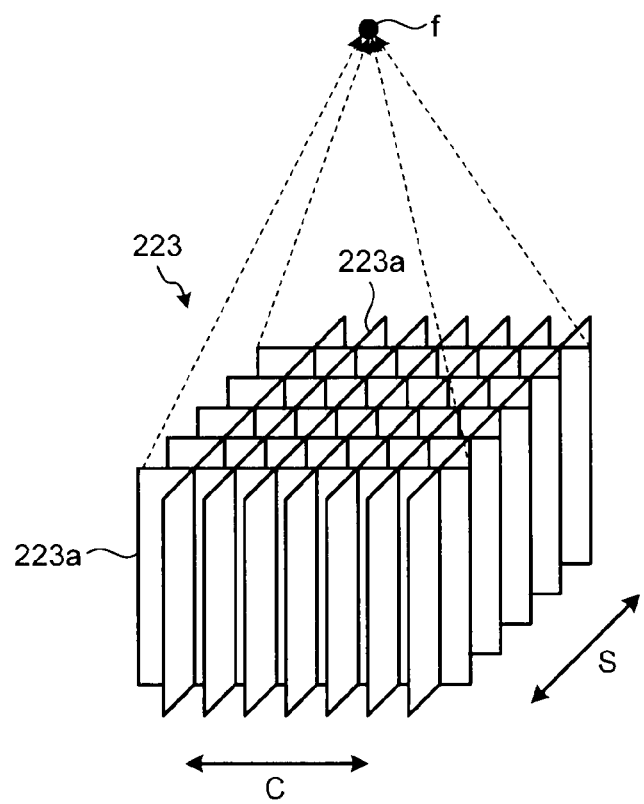
FIGS. 4 to 7 are diagrams of a configuration of a collimator module in FIG. 2.

Specifically, as shown in FIG. 4, the collimator module 223 includes collimator plates 223a, which are arrayed in a grid so as to be aligned in the channel direction and the slice direction. For example, 24 lines of the collimator plates 223a are arranged in the channel direction and 64 lines of the collimator plates 223a are arranged in the slice direction.

The plurality of collimator plates 223a of each of the collimator modules 223 have a thickness equal to that of the collimator plates 222a of the collimator base 222. FIG. 4 shows the plurality of collimator plates 223a aligned in parallel along the channel direction and the slice direction. In practice, each of the collimator plates 223a is arranged so as to face the focal point f of the X-ray tube 111. Because each of the collimator modules 223 is created as a small unit, inconsistency in the pitch of the collimator plates 223a due to a manufacturing error is small.

Figure 5:
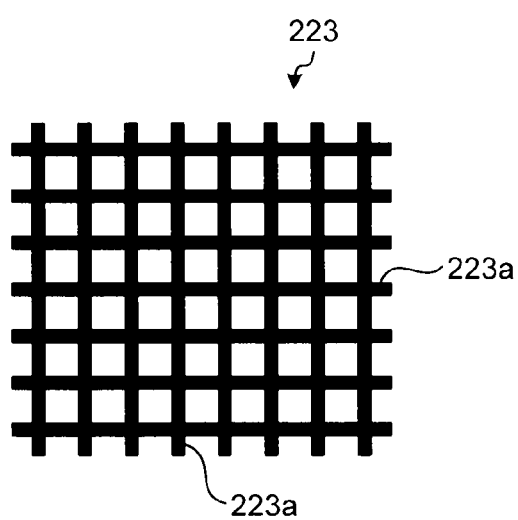

As shown in FIG. 5, the collimator plates 223a are arranged so as to be orthogonal to one another inside with respect to the ends of the collimator plates 223a. In other words, the collimator plates 223a have no frame surrounding them on all four sides and are formed such that the ends of each of the collimator plates 223a protrude on all four sides.

Figure 6:
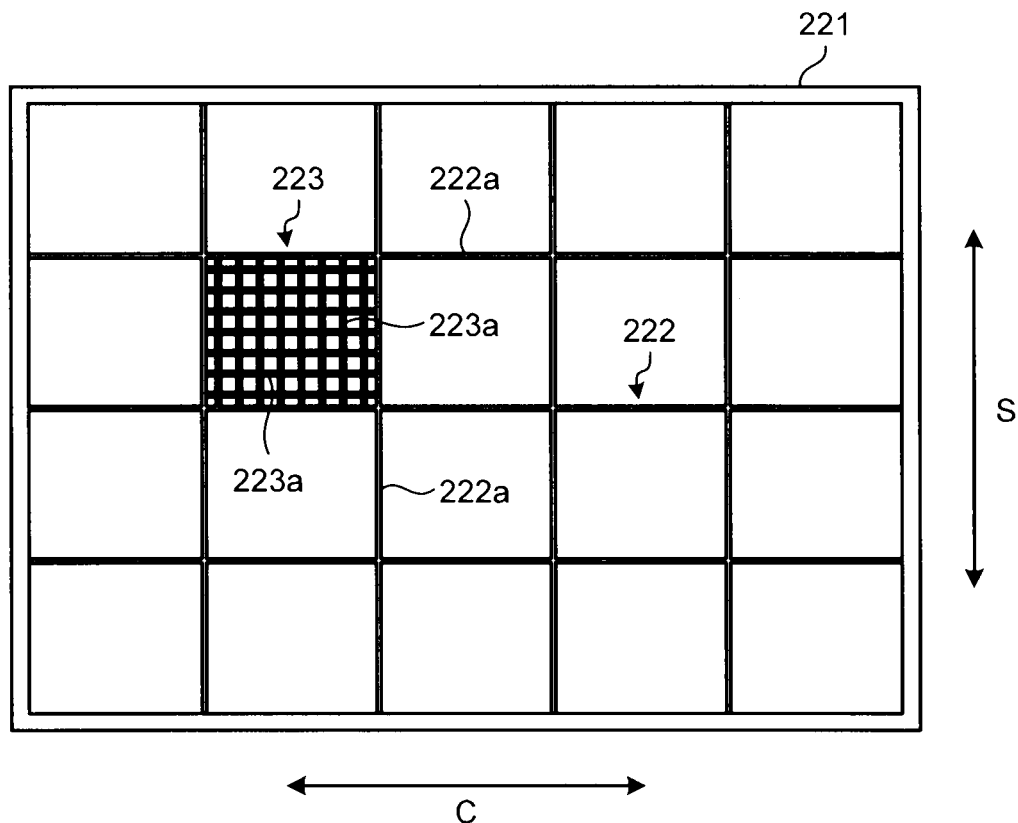
Figure 7:
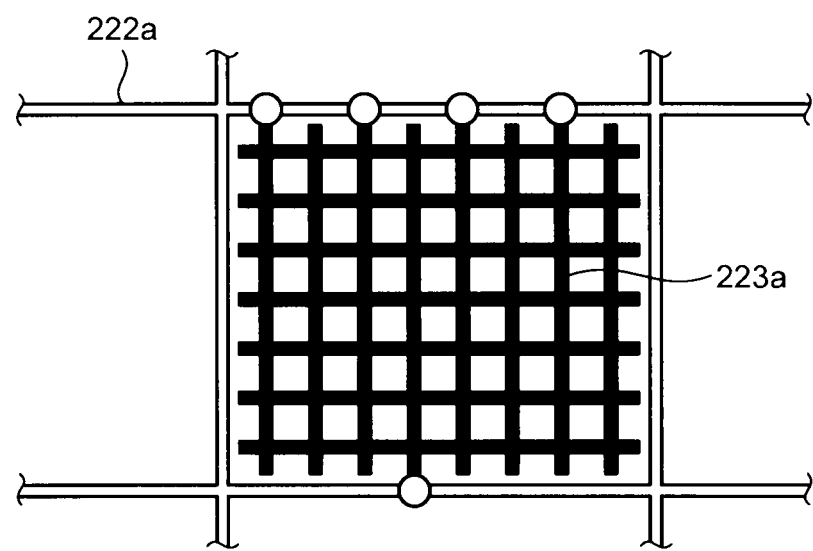

As shown in FIG. 6, the collimator plates 223a are formed such that, when the collimator modules 223 are arranged in the sections partitioned by the collimator plates 222a of the collimator base 222, the ends of the collimator plates 223a make contact with the surfaces of the collimator plates 222a. Accordingly, the collimator plates 222a of the collimator base 222 function as outer frames of the collimator modules 223. The adjacent collimator modules 223 are separated by the collimator plates 222a having a thickness equal to that of the collimator plates 223a. This separation is so that the thickness of the collimator plates is continuous even in the positions where the collimator modules 223 meet.

As shown in FIG. 6, because the collimator modules 223 are arranged respectively in the sections partitioned by the collimator plates 222a, the collimator modules 223 are arrayed accurately in the channel direction and the slice direction. This prevents inconsistency in the pitch between the collimator modules.

The ends of the collimator plates 223a are fixed to the surfaces of the collimator plates 222a of the collimator base 222 with, for example, an adhesive. For example, as shown in the upper part of FIG. 7, the ends of alternate collimator plates 223a may be fixed to surfaces of the collimator plates 222a. Alternatively, as shown in the lower part in FIG. 7, the ends of any one of the collimator plates 223a may be fixed.

As described above, the X-ray CT apparatus 100 according to the first embodiment includes the X-ray detector 210 that detects X-rays, which have been transmitted through the subject; and the collimator unit 220 that eliminates scattered radiation from X-rays that are incident on the X-ray detector 210. The collimator unit 220 includes the collimator base 222 that includes the plurality of collimator plates 222a arrayed in a grid so as to be aligned in the channel direction and the slice direction, which are orthogonal to each other; and the plurality of collimator modules 223 that include the plurality of collimator plates 223a arrayed in a grid so as to be aligned in the channel direction and the slice direction. The plurality of collimator plates 223a of each of the collimator modules 223 have a thickness equal to that of the collimator plates 222a, the collimator plates 223a are arranged so as to be orthogonal to one another on the inner side with respect to the ends of the collimator plates 223a, and the plurality of collimator plates 223a are formed such that, when the collimator modules 223 are arranged in the sections, the ends of the collimator plates 223a make contact with the surfaces of the collimator plates 222a.

In other words, because the collimator plates 222a of the collimator base 222 and the collimator plates 223a of the collimator modules 223 have an equal thickness, the thickness of the collimator plates is uniform in the whole collimator unit 220. Furthermore, because the collimator modules 223 are arrayed accurately in the channel direction and the slice direction with respect to the collimator base 222, the pitch of the collimator plates is uniform in the whole collimator unit 220. Thus, according to the first embodiment, the collimator with uniform thickness and pitch can be obtained. Furthermore, because the volume of scattered radiation to be eliminated is uniform between the channels and slices, an image with small artifacts can be obtained.

In the first embodiment, the plurality of collimator plates 222a of the collimator base 222 are each formed in an arc and are arranged such that the centers of the arcs coincide at the focal point f of the X-ray tube 111, which generates X-rays. Thus, according to the first embodiment, when the collimator modules 223 are arranged respectively in the sections partitioned by the collimator plates 222a, each of the collimator modules 223 faces the focal point f. In other words, the two-dimensional collimator modules 223 can be accurately arrayed so as to face the focal point f.

Second Embodiment

Figure 8:
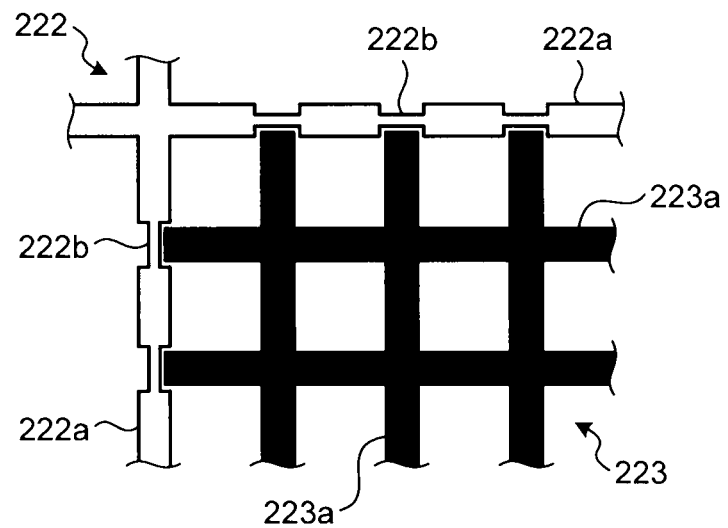
FIG. 8 is a diagram illustrating a method of fixing a collimator module according to a second embodiment.

A second embodiment will be described below. In the second embodiment, an example of a method of fixing the collimator module 223 described in the first embodiment will be described. FIG. 8 is a diagram of a method of fixing the collimator module 223 according to the second embodiment.

As shown in FIG. 8, in the second embodiment, a plurality of grooves 222b are formed on the surfaces of the collimator plates 222a of the collimator base 222 along the direction in which X-rays are incident. When the collimator module 223 is arranged in a section that is partitioned by the collimator plates 222a, the ends of the collimator plates 223a of the collimator module 223 make contact with the grooves 222b. The ends of the collimator plates 223a make contact with the grooves 222b, which are formed on the collimator plates 222a, and thus the collimator module 223 is positioned in the section partitioned by the collimator plates 222a.

An equal number of grooves 222b to that of the collimator plates 223a of the collimator module 223 may be formed or a smaller number of grooves 222b than that of the collimator plates 223a of the collimator module 223 may be formed. In other words, it is satisfactory if at least one groove 222b be formed. The grooves 222b may be formed on all four plate surfaces that surround the section in which the collimator module 223 is arranged. Alternatively, the grooves 222b may be formed on a single plate surface, two plate surfaces, or three plate surfaces.

As described above, according to the second embodiment, because the collimator modules 223 are positioned by the grooves 222b that are formed on the plate surfaces of the collimator plates 222a of the collimator base 222, each of the collimator modules 223 can be fixed accurately.

Third Embodiment

Figure 9:
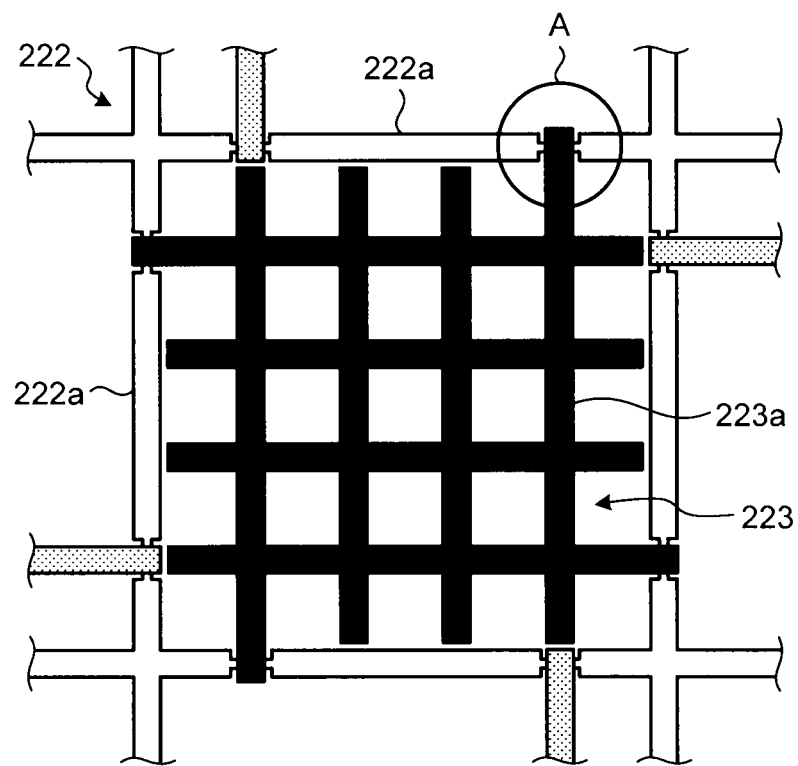
FIGS. 9 and 10 are diagrams illustrating a method of fixing a collimator module according to a third embodiment.
Figure 10:
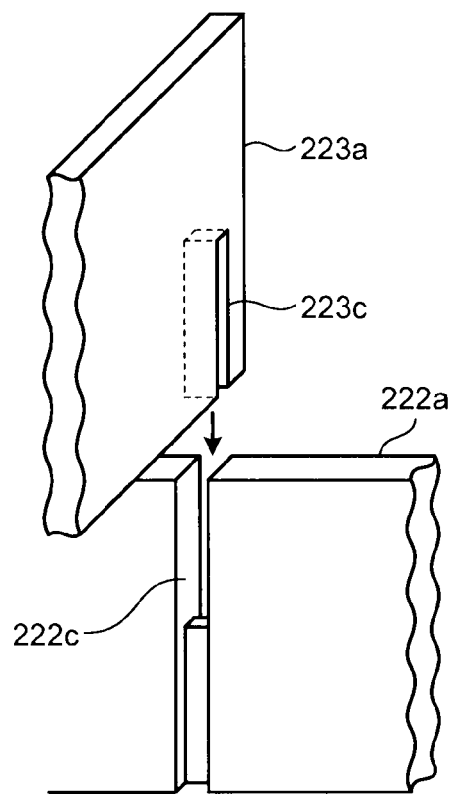

A third embodiment will be described below. In the third embodiment, another example of the method of fixing the collimator module 223 described in the first embodiment, which is different from that of the second embodiment, will be described. FIGS. 9 and 10 are diagrams of the method of fixing the collimator module 223 according to the third embodiment.

As shown in FIG. 9, in the third embodiment, when the collimator module 223 is arranged in a section partitioned by the collimator plates 222a, the ends of the collimator plates 223a engage with a part of the collimator plates 222a (see the part within the circle A in FIG. 9).

Specifically, in the third embodiment, engaging portions are formed on the ends of the collimator plates 223a of the collimator module 223. In addition, engaged portions that are engaged with the engaging portions formed on the ends of the collimator plates 223a are formed in the collimator plates 222a of the collimator base 222. When the collimator module 223 is arranged in a section partitioned by the collimator plates 222a, the engaging portions, which are formed on the ends of the collimator plates 223a, engage with the engaged portions of the collimator plates 222a. As described above, the ends of the collimator plate 223a engage with a part of the collimator plates 222a and thus the collimator module 223 is positioned in the section partitioned by the collimator plates 222a.

For example, as shown in FIG. 10, cutout portions 223c are formed as engaging portions on the ends of the collimator plates 223a of the collimator module 223. Furthermore, cutout portions 222c that can be engaged with the cutout portions 223c of the collimator plates 223a are formed as engaged portions in the collimator plates 222a of the collimator base 222.

The case is described above in which the engaging portions and the engaged portions are cutout portions. However, the shape of the engaging portions and the engaged portions is not limited to this. For example, protrusions may be formed on the ends of the collimator module 223 and holes that fit to the protrusions of the collimator module 223 may be formed on the surfaces of the collimator plates 222a of the collimator base 222.

The engaging portions and the engaged portions may be formed on all or a part of the ends of the collimator plates 223a of the collimator module 223. In other words, it is satisfactory if engaging portions and engaged portions be formed with respect to at least one of the ends of the plurality of collimator plates 223a.

As described above, according to the third embodiment, the engaging portions, which are formed on the ends of the collimator plates 223a of the collimator module 223, engage with the engaged portions, which are formed in the collimator plates 222a of the collimator base 222, and thus the collimator modules 223 is positioned. Accordingly, each of the collimator modules 223 can be fixed accurately. Furthermore, each of the collimator modules 223 can be positioned even if the collimator plates 223a are thin so that grooves cannot be formed on the surfaces of the collimator plates 223a.

Fourth Embodiment

Figure 11:
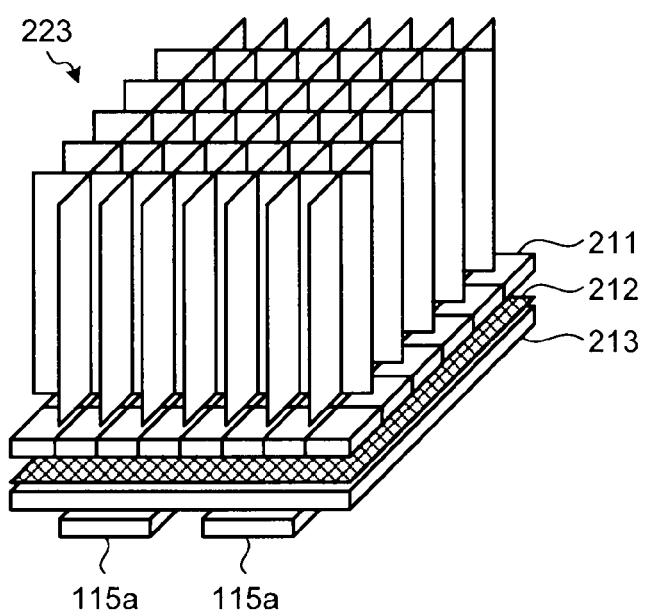
FIG. 11 is a diagram of an X-ray detector and a collimator module according to a fourth embodiment.

A fourth embodiment will be described below. In the fourth embodiment, a case will be described in which the X-ray detector 210 described in the first embodiment is divided into a plurality of parts and each of the divided parts is combined with the collimator module 223 into a module. FIG. 11 is a diagram of the X-ray detector and the collimator module 223 according to the fourth embodiment.

In the fourth embodiment, the X-ray detector 210 is divided into parts each having a size corresponding to that of the collimator module 223. In other words, the X-ray detector 210 is divided into a plurality of blocks corresponding respectively to the plurality of sections that are partitioned by the collimator plates 222a of the collimator base 222. The divided blocks are attached to the collimator modules 223, respectively.

Specifically, as shown in FIG. 11, a block 211 that is obtained by dividing the scintillator array, a block 212 that is obtained by dividing the PD array, and a block 213 that is obtained by dividing the circuit substrate are attached to the collimator modules 223. Accordingly, the collimator module 223 and the block of the X-ray detector 210 function as a module. Furthermore, as shown in FIG. 11, a block 115a that is obtained by dividing the DAS 115 may be combined with the collimator module 223 and the block of the X-ray detector 210 into a module.

As described above, according to the fourth embodiment, a part of the X-ray detector 210 or a part of the X-ray detector 210 and the DAS 115 is combined with the collimator module 223 into a module. Accordingly, even if the X-ray detector 210 or the DAS 115 is partly damaged, the damage can be recovered easily by replacing the block containing the damaged part. Furthermore, because the size of the X-ray detector or the DAS can be changed easily by reducing or increasing the number of modules, scalability of developing the X-ray detector or the DAS can be increased.

In the first to fourth embodiments, the collimator frame 221 functions as a supporter that supports the plurality of collimator modules 223 such that the collimator modules 223 are aligned in the plurality of straight lines along the channel direction and in the plurality of straight lines along the slice direction. The collimator base 222 is provided to the collimator frame 221, which functions as the supporter, and the collimator base 222 functions as a fixing unit that fixes the positions of the plurality of collimator modules 223 in the channel direction and the slice direction.

The supporter and the fixing unit are not limited to the units described in the first to fourth embodiments and various shapes may be used. Here, other examples of the supporter and the fixing unit will be described. Parts having the same functions as those of the above-described embodiments are denoted by the same reference numbers and detailed descriptions for those parts will be omitted below.

Fifth Embodiment

Figure 12:
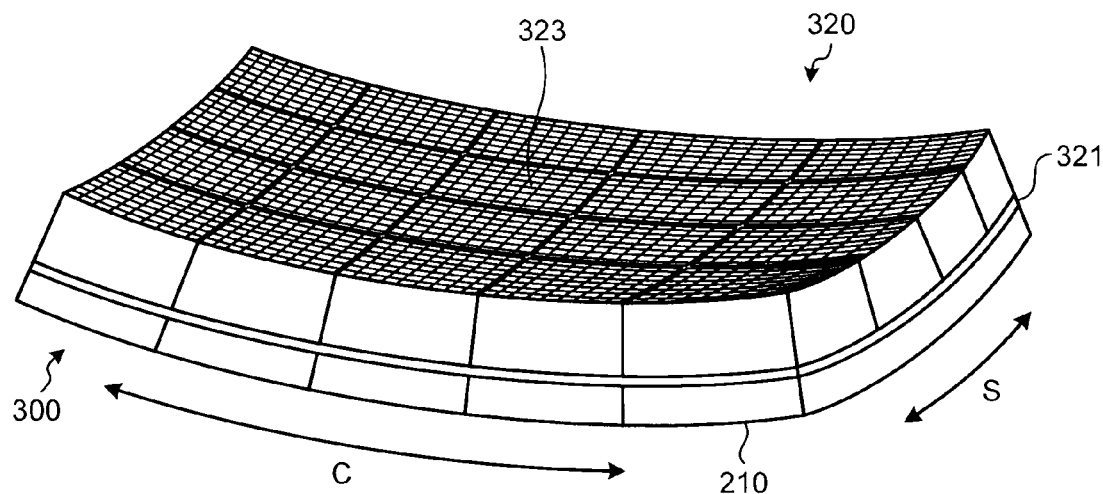
FIG. 12 is a diagram of a collimator unit according to a fifth embodiment.

A fifth embodiment will be described first. In the fifth embodiment, a case will be described in which a plate-shaped member is used as a supporter. FIG. 12 is a diagram of a collimator unit 320 according to the fifth embodiment. As shown in FIG. 12, in the fifth embodiment, the collimator unit 320 of an X-ray detector 300 includes a collimator support plate 321 and a plurality of collimator modules 323. Each of the collimator modules 323 are arranged on the X-ray detector 210 via the collimator support plate 321.

The collimator support plate 321 is formed to have a shape of a plate that curves along a sphere about the focal point of X-rays. The collimator support plate 321 supports the plurality of collimator modules 323 such that the collimator modules 323 are aligned on a surface of the collimator support plate 321 on the side to which X-rays are applied. The collimator support plate 321 supports the plurality of collimator modules such that the collimator modules are aligned in a plurality of straight lines along the channel direction (direction denoted by the arrow C) and in a plurality of straight lines along the slice direction (direction denoted by the arrow S). The collimator support plate 321 is formed of a material, such as glass epoxy, that has a low X-ray absorption coefficient.

Figure 13:
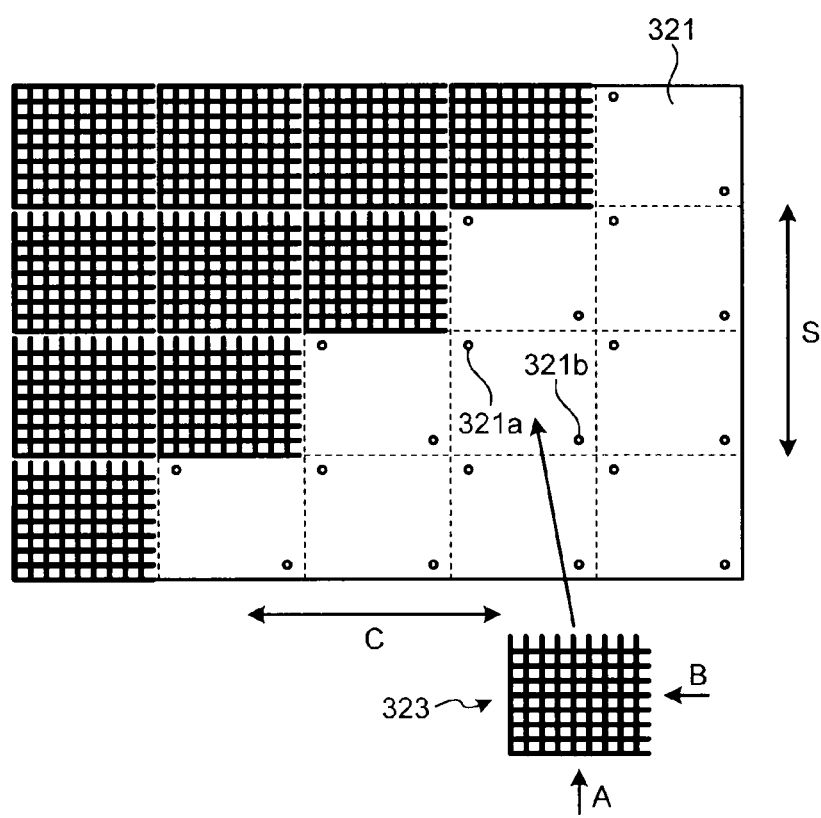
FIGS. 13 to 15 are diagrams of configurations of a collimator support plate and a collimator module according to a fifth embodiment.
Figure 14:
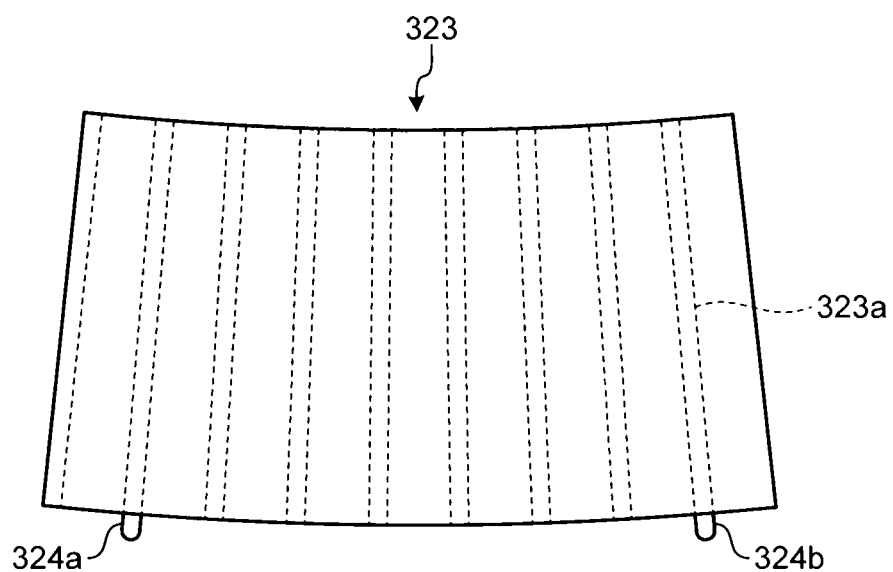
Figure 15:
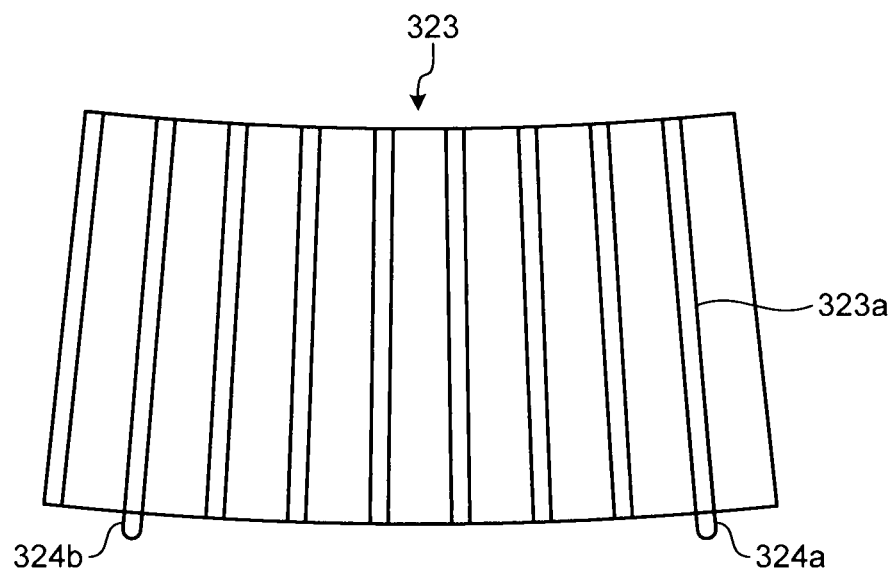

The collimator modules 323 eliminate scattered radiation from X-rays that are incident on the X-ray detector 210. FIGS. 13 to 15 are diagrams of configurations of the collimator support plate 321 and the collimator modules 323 according to the fifth embodiment. FIG. 13 is a top view of the collimator support plate 321 and the collimator modules 323. FIG. 14 is a side view of the collimator module 323 viewed from the direction indicated by the arrow A in FIG. 13. FIG. 15 is a side view of the collimator module 323 viewed from the direction indicated by the arrow B in FIG. 13.

As shown in FIG. 13, the collimator modules 323 are arranged so as to be aligned in a plurality of parallel straight lines aligned at regular intervals along the channel direction (direction denoted by the arrow C) and in a plurality of parallel straight lines aligned at regular intervals along the slice direction (direction denoted by the arrow S). In the fifth embodiment, collimator modules each having outer frames on two sides as shown in the lower part in FIG. 13 are used.

On the surface of the collimator support plate 321 on which the plurality of collimator modules 323 are arranged, engaging portions that engage with engaged portions, with which each of the collimator modules 323 is provided, are formed for each section in which each collimator module 323 is placed (sections indicated by the dotted lines in FIG. 13). In the fifth embodiment, for example, engaging recesses 321a and 321b are formed as engaging portions on both ends on one diagonal line in each section of the collimator support plate 321.

Furthermore, as shown in FIGS. 14 and 15, the collimator module 323 includes a plurality of collimator plates 323a, which are arrayed in a grid so as to be aligned in the channel direction and the slice direction. The plurality of the collimator plates 323a of each of the collimator modules 323 have all the same thickness, and are arranged so as to face the focal point f of the X-ray tube 111.

Engaged portions that are engaged with the engaging portions that are formed on the collimator support plate 321 are formed on the collimator modules 323. In the fifth embodiment, for example, as shown in FIGS. 14 and 15, engaging protrusions 324a and 324b are provided as engaged portions on both ends on one diagonal line on the bottom of each of the collimator modules 323. The engaging protrusion 324b is provided in the position where it engages with the engaging recess 321b, when the collimator module 323 is placed in a section of the collimator support plate 321.

The engaging protrusions 324a and 324b of each of the collimator modules 323 engage with the engaging recesses 321a and 321b that are formed in each of the sections of the collimator support plate 321; therefore the collimator modules 323 are fixed to the collimator support plate 321 so as to be are aligned on the plurality of straight lines along the channel direction and on the plurality of straight lines along the slice direction.

As described above, in the fifth embodiment, the collimator support plate 321 that functions as the supporter is formed to have a shape of a plate that curves along a sphere about the focal point of X-rays and the collimator support plate 321 supports the plurality of collimator modules 323 such that the collimator modules 323 are aligned on the surface of the collimator support plate 321 on the side to which X-rays are applied. Furthermore, the fixing unit includes the plurality of engaging recesses 321a and 321b, which are provided on the surface of the collimator support plate 321, which is the surface on which the plurality of collimator modules 323 are arranged. The engaging recesses engage respectively with the engaging protrusions 324a and 324b, with which the collimator modules 323 are provided, and thus the positions of the plurality of collimator modules 323 are fixed. Accordingly, according to the fifth embodiment, by using the plate-shaped member as the supporter, a collimator with uniform thickness and pitch of collimator plates can be obtained with a simple configuration.

In the fifth embodiment, the case is described in which the engaging recesses are formed in the collimator support plate 321 and the engaging protrusions are provided to the collimator modules 323. However, the embodiment of the fixing unit is not limited to this. For example, the engaging protrusions may be provided to the collimator support plate 321 and the engaging recesses may be formed in the collimator modules 323.

Sixth Embodiment

A sixth embodiment will be described below. In the sixth embodiment, an example will be described in which a plate-shaped member is used as a supporter as in the case of the fifth embodiment and a fixing unit having a different shape is used. In the sixth embodiment, the collimator unit includes a collimator support plate 421 and a plurality of collimator modules 423. Each of the collimator modules 423 is arranged on the X-ray detector 210 via the collimator support plate 421.

As in the case of the collimator support plate 321 in FIG. 12, the collimator support plate 421 is formed into a shape of a plate that curves along a sphere about the focal point of X-rays. The collimator support plate 421 supports the plurality of collimator modules 423 such that the plurality of collimator modules 423 are aligned on the surface of the collimator support plate 421 on the side to which X-rays are applied. The collimator support plate 421 supports the plurality of collimator modules such that the plurality of collimator modules are aligned in a plurality of straight lines along the channel direction (direction denoted by the arrow C) and in a plurality of straight lines along the slice direction (direction denoted by the arrow S). The collimator support plate 421 is formed of a material, such as glass epoxy, that has a low X-ray absorption coefficient.

Figure 16:
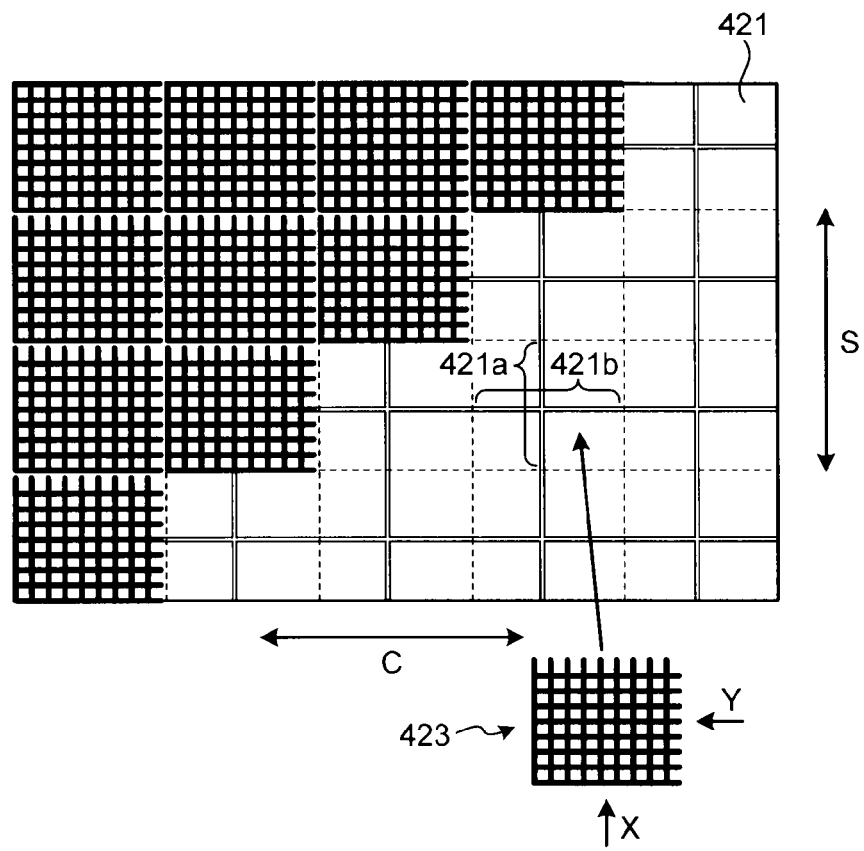
FIGS. 16 to 18 are diagrams of configurations of a collimator supporter and a collimator module according to a sixth embodiment.
Figure 17:
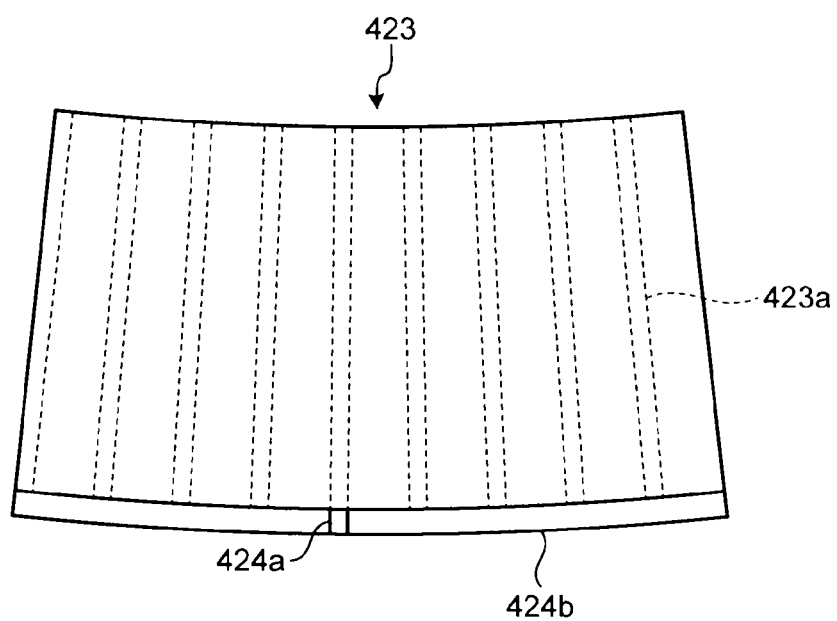
Figure 18:
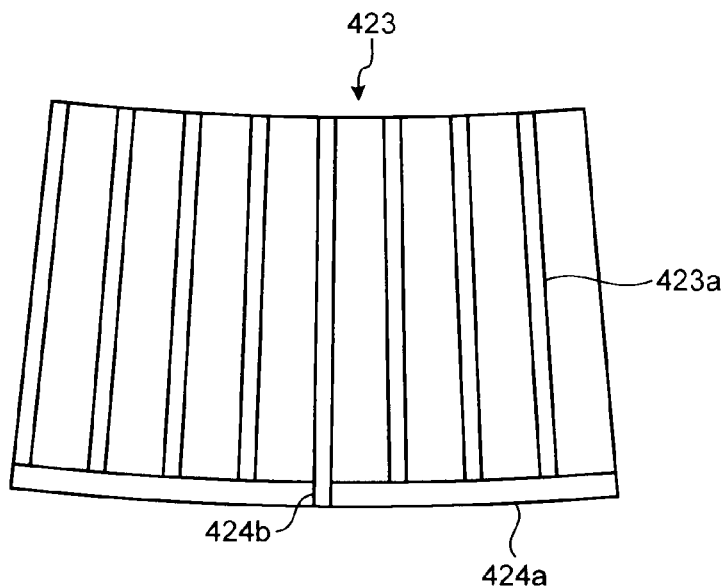

The collimator modules 423 eliminate scattered radiation from X-rays that are incident on the X-ray detector 210. FIGS. 16 to 18 are diagrams of configurations of the collimator support plate 421 and the collimator modules 423 according to the sixth embodiment. FIG. 16 is a top view of the collimator support plate 421 and the collimator modules 423. FIG. 17 is a side view of the collimator module 423 viewed from the direction indicated by the arrow A in FIG. 16. FIG. 18 is a side view of the collimator module 423 viewed from the direction indicated by the arrow B in FIG. 16.

As shown in FIG. 16, as in the case of the fifth embodiment, the collimator modules 423 are arranged so as to be aligned in a plurality of parallel straight lines aligned at regular intervals along the channel direction (direction denoted by the arrow C) and in a plurality of parallel straight lines aligned at regular intervals along the slice direction (direction denoted by the arrow S). In the sixth embodiment, as well, collimator modules each having outer frames on two sides as shown in the lower part in FIG. 16 are used.

On the surface of the collimator support plate 421 on which the plurality of collimator modules 423 are arranged, engaging portions which engage with engaged portions, with which each of the collimator modules 423 is provided, are formed for each section in which each collimator module 423 is placed (sections indicated by the dotted lines in FIG. 16). In the sixth embodiment, grooves 421a and 421b that are formed in a cross shape are formed as engaging portions in each section of the collimator support plate 421.

Furthermore, as shown in FIGS. 17 and 18, the collimator module 423 includes a plurality of collimator plates 423a, which are arrayed in a grid so as to be aligned in the channel direction and the slice direction. The plurality of the collimator plates 423a of each of the collimator modules 423 have all the same thickness, and are arranged so as to face the focal point f of the X-ray tube 111.

Engaged portions that are engaged with the engaging portions formed in the collimator support plate 421 are formed on the collimator modules 423. In the sixth embodiment, for example, as shown in FIGS. 17 and 18, cross protrusions 424a and 424b in a cross shape are formed as engaged portions on the bottom of each of the collimator modules 423. The protrusion 424a is provided in the position where it is engaged with the groove 421a when the collimator module 423 is placed in a section of the collimator support plate 421. The protrusion 424b is provided in the position where it is engaged with the groove 421b when the collimator module 423 is placed in a section of the collimator support plate 421.

The protrusion 424a is achieved by forming one of the plurality of collimator plates 423a of the collimator module 423 along the slice direction so as to have a larger thickness in the direction in which X-rays are applied than that of other collimator plates. In other words, the protrusion 424a is formed by protruding the end of one of the collimator plates 423a, which are aligned in the channel direction, more than the ends of other collimator plates as shown in FIG. 17. For example, the protrusion 424a is formed by protruding the end of the collimator plate that passes through the center part of the collimator module 423.

Similarly, the protrusion 424b is achieved by forming one of the plurality of collimator plates 423a of the collimator module 423 along the channel direction so as to have a larger thickness in the direction in which X-rays are applied than that of other collimator plates. In other words, the protrusion 424b is formed by protruding the end of one of the collimator plates 423a, which are aligned in the slice direction, more than the ends of other collimator plates as shown in FIG. 18. The protrusion 424b is formed by, for example, protruding the end of the collimator plate that passes through the center part of the collimator module 423.

The protrusions 424a and 424b of each of the collimator modules 423 are engaged with the grooves 421a and 421b that are formed in each of the sections of the collimator support plate 421. Accordingly, each of the collimator modules 423 is fixed to the collimator support plate 421 so as to be aligned on the plurality of straight lines along the channel direction and on the plurality of straight lines along the slice direction.

As described above, in the sixth embodiment, the collimator support plate 421 that functions as the supporter is formed to have a shape of a plate that curves along the sphere about the focal point of X-rays and the collimator support plate 421 supports the plurality of collimator modules 423 such that the collimator modules 423 are aligned on the surface on the side to which X-rays are applied. Furthermore, the fixing unit includes the plurality of grooves 421a and 421b that are provided on the surface of the collimator support plate 421, which is the surface on which the plurality of collimator modules 423 are arranged. The grooves engage respectively with the protrusions 424a and 424b, with which each of the collimator modules 423 is provided, and thus the positions of the plurality of collimator modules 423 are fixed. Accordingly, according to the sixth embodiment, by using the plate-shaped member as the supporter, a collimator with uniform thickness and pitch of collimator plates can be obtained with a simple configuration.

In the fifth embodiment, the case is described in which the grooves are provided to the collimator support plate 421 and the protrusions are provided to the collimator modules 423. However, the embodiment of the fixing unit is not limited to this. For example, the protrusions may be provided to the collimator support plate 421 and the grooves may be formed in the collimator modules 423.

Seventh Embodiment

Figure 19:
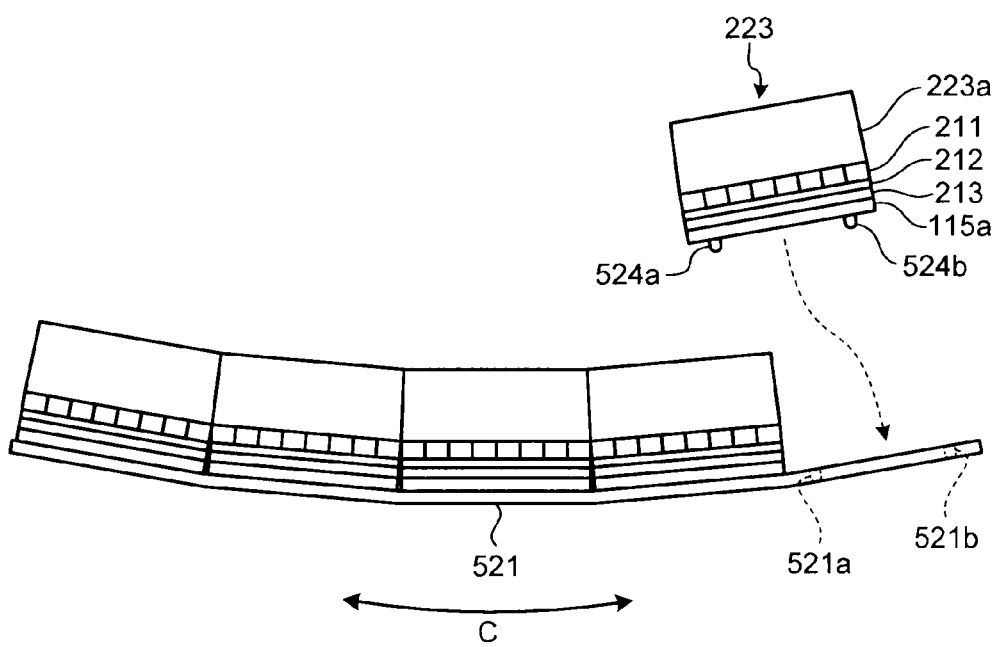
FIG. 19 is a diagram of configurations of a collimator supporter and a collimator module according to a seventh embodiment.
Figure 20:
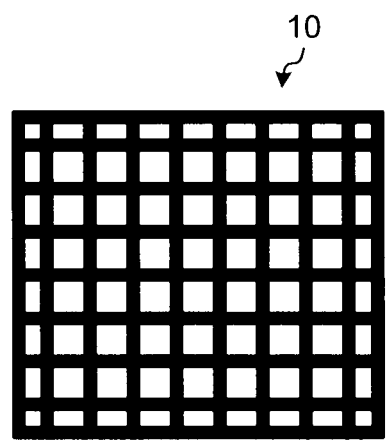
FIGS. 20 to 23 are diagrams illustrating a problem in conventional technology.
Figure 21:
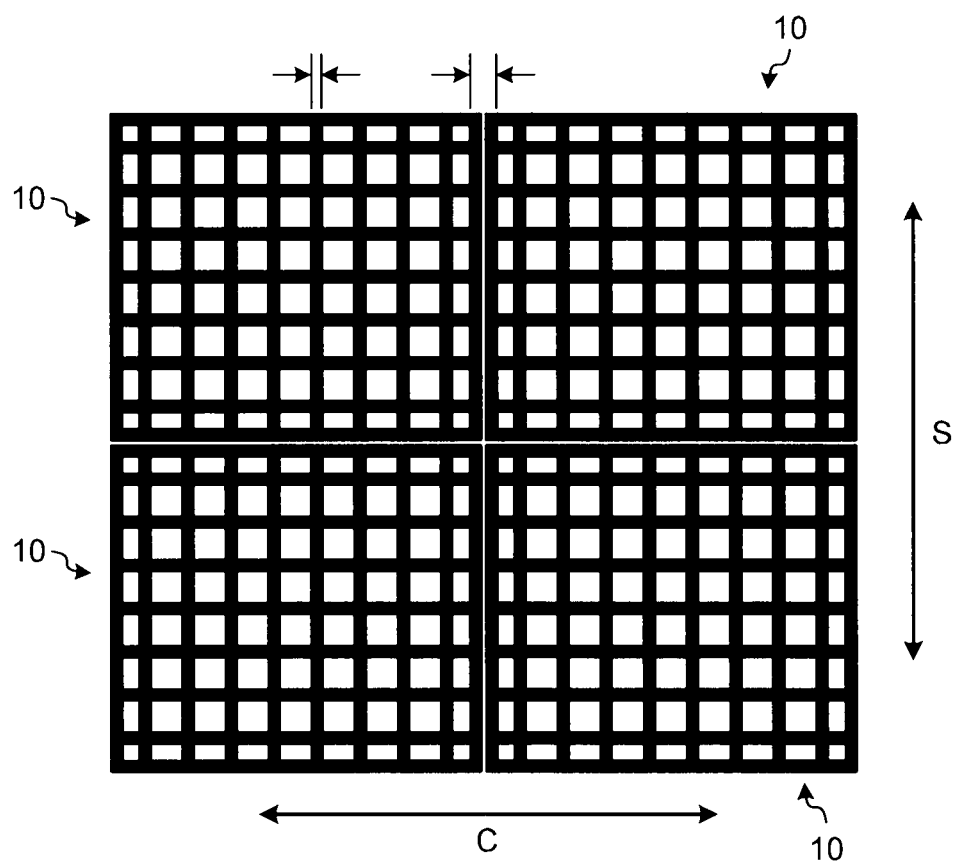
Figure 22:
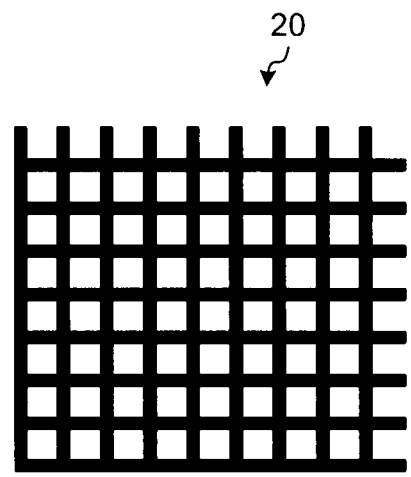
Figure 23:
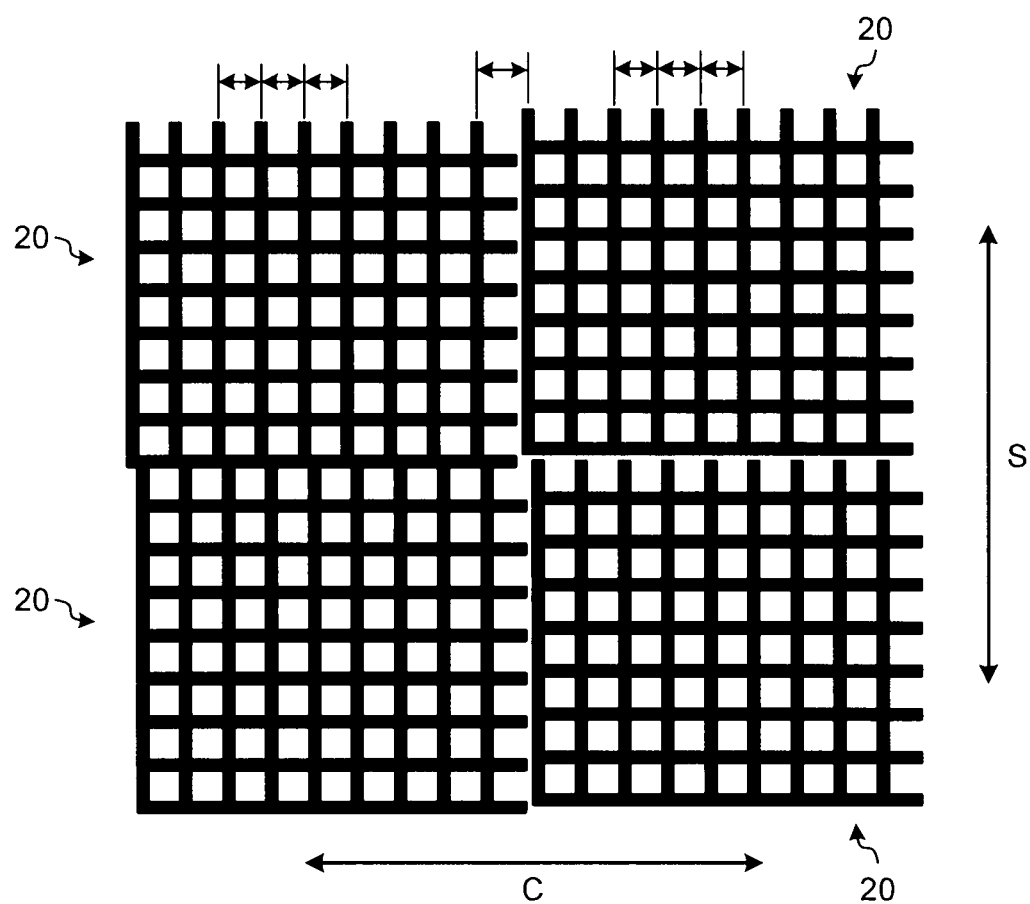

A seventh embodiment will be described. In the seventh embodiment, an example will be described in which a plate-shaped member is used as a supporter as in the case of the fifth and sixth embodiments and the X-ray detector 210 and the collimator module 223 function as a module as described in the fourth embodiment. FIG. 19 is a diagram of configurations of a collimator support plate 521 and the collimator modules 223 according to the seventh embodiment. FIG. 19 is a side view of the collimator support plate 521 and the collimator modules 223 viewed from the slice direction.

As shown in FIG. 19, in the seventh embodiment, the collimator modules 223 are used each functioning, with a block of the X-ray detector 210, as a module. Specifically, as shown in FIG. 11, the block 211 that is obtained by dividing the scintillator array, the block 212 that is obtained by dividing the PD array, the block 213 that is obtained by dividing the circuit substrate, and the block 115a that is obtained by dividing the DAS 115 are attached to the collimator module 223.

As shown in FIG. 19, as in the case of the fifth and sixth embodiments, the collimator support plate 521 is formed to have a shape of a plate that curves along a sphere about the focal point of X-rays. The collimator support plate 521 supports the plurality of collimator modules 223 such that the collimator modules 223 are aligned on a surface of the collimator support plate 421 on the side to which X-rays are applied. The collimator support plate 521 supports the plurality of collimator modules such that the collimator modules are aligned in a plurality of straight lines along the channel direction (direction denoted by the arrow C) and in a plurality of straight lines along the slice direction (direction denoted by the arrow S).

On the surface of the collimator support plate 521 on which the plurality of collimator modules 223 and each block of the X-ray detector 210 are arranged, engaging portions that engage with engaged portions, with which the block of the X-ray detector 210 attached to each of the collimator modules 223 is provided, are formed for each section in which each collimator module 223 is placed. In the seventh embodiment, for example, engaging recesses 521a and 521b like the engaging recesses 321a and 321b shown in FIG. 13 are formed on one diagonal line in each section of the collimator support plate 521.

On the other hand, engaged portions that are engaged with the engaging portions, which are formed in the collimator support plate 521, are formed on the block of the X-ray detector 210 that is attached to the collimator module 223. In the seventh embodiment, for example, as shown in FIG. 19, engaging protrusions 524a and 524b like the engaging protrusions 324a and 324b in FIGS. 14 and 15 are provided as engaged portions on both ends on one diagonal line on the bottom of the block 115a obtained by dividing the DAS 115. The engaging protrusion 524a is provided in the position where it engages with the engaging recess 521a when the collimator module 223 and the block of the X-ray detector 210 are placed in a section of the collimator support plate 521. The engaging protrusion 524b is provided in the position where it engages with the engaging recess 521b when the collimator module 223 and the block of the X-ray detector 210 are placed in the section of the collimator support plate 521.

The engaging protrusions 524a and 524b of each block of the X-ray detector 210 are engaged with the engaging recesses 521a and 521b, which are formed in each of the sections of the collimator support plate 521, and thus the collimator modules 223 are fixed to the collimator support plate 521 so as to be aligned on the plurality of straight lines along the channel direction and on the plurality of straight lines along the slice direction.

As described above, in the seventh embodiment, the X-ray detector 210 is divided into an equal number of a plurality of blocks to that of the plurality of collimator modules 223 and the blocks are attached to the plurality of collimator modules 223, respectively. The collimator support plate 521 functioning as the supporter is formed to have a shape of a plate that curves along the sphere about the focal point of X-rays and the collimator support plate 521 supports, via the blocks of the X-ray detector 210, the plurality of collimator modules 223 such that the collimator modules 223 are aligned on the surface on the side to which X-rays are applied. Furthermore, the fixing unit includes the plurality of engaging recesses 521a and 521b, which are provided on the surface of the collimator support plate 521, which is the surface on which the plurality of collimator modules 223 and the blocks of the X-ray detector 210 are arranged. The engaging recesses engage respectively with the engaging protrusions, with which each of the blocks of the X-ray detector 210 is provided, and thus the positions of the plurality of collimator modules 223 are fixed. Accordingly, according to the seventh embodiment, because no collimator support plate is arranged between the collimator modules and the X-ray detector, a collimator with uniform thickness and pitch of collimator plates can be obtained with a simple configuration without reducing the accuracy in detecting X-rays.

In the seventh embodiment, the case is described in which the engaging recesses are formed in the collimator support plate 521 and the engaging protrusions are provided to the collimator modules 223. However, the embodiment of the fixing unit is not limited to this. For example, the engaging protrusions may be provided to the collimator support plate 521 and the engaging recesses may be formed in the collimator modules 223.

In the first to seventh embodiments, X-ray CT apparatuses and X-ray detectors are descried. However, the technology described in the above embodiments may be similarly applied to other radiation diagnostic apparatuses, such as X-ray diagnostic apparatuses and PETs. In other words, the collimator units described in the above embodiments can be applied to radiation diagnostic apparatuses that include a radiation detector that detects radiation that has passed through a subject; and a collimator unit that eliminates scattered radiation from radiation that is incident on the radiation detector.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   an X-ray tube configured to generate X-rays;
   an X-ray detector configured to detect X-rays that have passed through a subject; and
   a collimator unit provided above the X-ray detector,
   wherein the collimator unit includes:
   a plurality of collimator modules each configured to include a plurality of first collimator plates arranged in a grid along a channel direction and a slice direction that are orthogonal to each other, the collimator modules each including therein an outer frame on at least one side of each collimator module and with the first collimator plates in a state that ends thereof protrude from at least another one side of each module; and
   a collimator support plate configured to fix the collimator modules respectively in a state of being aligned along the channel direction and the slice direction and in a state that the protruded ends of the first collimator plates of each collimator module contact with the outer frame of an adjacent collimator module.

2. The X-ray CT apparatus according to claim 1, further comprising:
   a supporter formed to have a shape of a plate that curves along a sphere about a focal point of the X-rays, and configured to support the collimator modules such that the collimator modules are aligned on a surface of the supporter on a side to which the X-rays are applied, wherein
   the fixing unit includes a plurality of engaging portions provided on the surface of the supporter on which the collimator modules are arranged and the engaging portions engage respectively with engaged portions that are provided to the collimator modules and thus the positions of the collimator modules are fixed.

3. The X-ray CT apparatus according to claim 2, wherein
   each of the engaging portions include at least two recesses formed on the surface of the supporter, and
   each of the engaged portions includes at least two protrusions formed on a corresponding collimator module and engages with the recesses when the corresponding collimator modules is placed on the supporter.

4. The X-ray CT apparatus according to claim 2, wherein
   each of the engaging portions is a cross-shaped groove formed on the surface of the supporter, and
   each of the engaged portions is a cross-shaped protrusion formed on a corresponding collimator module and engages with the groove when the corresponding collimator modules is placed on the supporter.

5. The X-ray CT apparatus according to claim 1, further comprising:
   a supporter formed to have a shape of a plate that curves along a sphere about a focal point of the X-rays, and configured to support the collimator modules such that the collimator modules are aligned on a surface of the supporter on a side to which the X-rays are applied, wherein
   the X-ray detector is divided into an equal number of a plurality of blocks to that of the collimator modules and the blocks are attached respectively to the collimator modules,
   the supporter is configured to support, via the blocks of the X-ray detector, the collimator modules, and
   the collimator support plate includes a plurality of engaging portions provided on the surface of the supporter on which the collimator modules and the blocks of the X-ray detector are arranged and the engaging portions engage respectively with engaged portions provided to the blocks of the X-ray detector and thus the positions of the collimator modules are fixed.

6. The X-ray CT apparatus according to claim 1, further comprising:
   a supporter formed to have a shape of a rectangle and depth in a direction in which the X-rays are applied and the supporter is configured to support the collimator modules such that the collimator modules are aligned within the rectangle.

7. The X-ray CT apparatus according to claim 1, wherein the first collimator plates of the collimator modules are arranged so as to be orthogonal to one another inside with respect to ends of the first collimator plates.

8. A radiation detector comprising:
   a detector configured to detect radiation that has passed through a subject; and
   a collimator unit provided above a radiation generator,
   wherein the collimator unit includes:
   a plurality of collimator modules each configured to include a plurality of first collimator plates arranged in a grid along a channel direction and a slice direction that are orthogonal to each other, the collimator modules each including therein an outer frame on at least one side of each collimator module and with the first collimator plates in a state that ends thereof protrude from at least another one side of each module; and
   a collimator support plate configured to fix the collimator modules respectively in a state of being aligned along the channel direction and the slice direction and in a state that the protruded ends of the first collimator plates of each collimator module contact with the outer frame of an adjacent collimator module.

9. A method of manufacturing a radiation detector including a detector configured to detect radiation and a collimator unit provided above a radiation generator, the method comprising:

forming a plurality of collimator modules each by arranging a plurality of first collimator plates in a grid along a channel direction and a slice direction that are orthogonal to each other, the collimator modules each including therein an outer frame on at least one side of each collimator module and with the first collimator plates in a state that ends thereof protrude from at least another one side of each module; and forming the collimator unit by fixing, by using a collimator support plate, the collimator modules respectively in a state of being aligned along the channel direction and the slice direction and in a state that the protruded ends of the first collimator plates of each collimator module contact with the outer frame of an adjacent collimator module.

10. An X-ray CT apparatus comprising:
a X-ray tube configured to generate X-rays;
an X-ray detector configured to detect X-rays that have passed through a subject; and
a collimator unit provided above the X-ray detector, wherein the collimator unit includes:
a plurality of collimator modules each configured to include a plurality of first collimator plates arranged in a grid along a channel direction and a slice direction that are orthogonal to each other, the collimator modules including therein with an outer frame on at least one side of each collimator module and with the first collimator plates in a state that ends thereof protrude from at least another one side of each module;
a supporter provided between the X-ray detector and the plurality of the collimator modules, and configured to support the plurality of the collimator modules; and
a collimator support plate configured to fix the collimator modules respectively in a state of being aligned along the channel direction and the slice direction on the supporter and in a state that the protruded ends of the first collimator plates of each collimator module contact with the outer frame of an adjacent collimator module.

* * * * *

UNITED STATES PATENT AND TRADEMARK OFFICE
CERTIFICATE OF CORRECTION

PATENT NO. : 9,320,476 B2
APPLICATION NO. : 13/239843
DATED : April 26, 2016
INVENTOR(S) : Machiko Iso et al.

It is certified that error appears in the above-identified patent and that said Letters Patent is hereby corrected as shown below:

On the title page, Item (73), the Assignee's information is incorrect. Item (73) should read:

--(73) Assignee: Toshiba Medical Systems Corporation, Otawara-shi, (JP)--

Signed and Sealed this
Nineteenth Day of July, 2016

Michelle K. Lee
*Director of the United States Patent and Trademark Office*